United States Patent [19]
Green et al.

[11] Patent Number: 5,878,937
[45] Date of Patent: Mar. 9, 1999

[54] APPARATUS FOR APPLYING SURGICAL FASTENERS

[75] Inventors: David T. Green, Westport; Henry Bolanos, East Norwalk; Keith Ratcliff, Sandy Hook; Lisa M. Heaton, Norwalk; John C. Robertson, Bloomfield, all of Conn.

[73] Assignee: United States Surgical Corporation, Norwalk, Conn.

[21] Appl. No.: 939,144

[22] Filed: Sep. 29, 1997

Related U.S. Application Data

[60] Continuation of Ser. No. 470,818, Jun. 6, 1995, abandoned, which is a division of Ser. No. 234,712, Apr. 28, 1994, Pat. No. 5,558,266, which is a continuation of Ser. No. 779,505, Oct. 18, 1991, abandoned.

[51] Int. Cl.⁶ ................................................ A61B 17/068
[52] U.S. Cl. ......................................................... 227/175.2
[58] Field of Search ............................ 227/175.2, 175.3, 227/175.4, 176.1, 179.1, 178.1, 19

[56] References Cited

U.S. PATENT DOCUMENTS

| | | |
|---|---|---|
| 804,229 | 11/1905 | Hutchinson . |
| 2,891,250 | 6/1959 | Hirata . |
| 3,080,564 | 3/1963 | Strekopitov et al. . |
| 3,252,643 | 5/1966 | Strekopytov et al. . |
| 3,269,630 | 8/1966 | Fleischer . |
| 3,692,224 | 9/1972 | Astafiev et al. . |
| 3,795,034 | 3/1974 | Strekopytov et al. . |
| 4,349,028 | 9/1982 | Green . |
| 4,354,628 | 10/1982 | Green . |
| 4,442,964 | 4/1984 | Becht . |
| 4,470,533 | 9/1984 | Schuler . |
| 4,506,670 | 3/1985 | Crossley . |
| 4,508,253 | 4/1985 | Green . |
| 4,513,746 | 4/1985 | Aranyi et al. . |
| 4,522,327 | 6/1985 | Korthoff et al. . |
| 4,527,724 | 7/1985 | Chow et al. . |
| 4,530,453 | 7/1985 | Green . |
| 4,566,620 | 1/1986 | Green et al. . |
| 4,573,622 | 3/1986 | Green . |
| 4,580,712 | 4/1986 | Green . |
| 4,585,153 | 4/1986 | Failla et al. . |
| 4,591,085 | 5/1986 | Di Giovanni . |
| 4,605,004 | 8/1986 | Di Giovanni et al. . |
| 4,606,344 | 8/1986 | Di Giovanni . |
| 4,606,345 | 8/1986 | Dorband et al. . |
| 4,607,636 | 8/1986 | Kula et al. . |
| 4,632,290 | 12/1986 | Green et al. . |
| 4,715,520 | 12/1987 | Roehr, Jr. et al. . |
| 4,728,020 | 3/1988 | Green et al. . |
| 4,754,909 | 7/1988 | Barker et al. ............................. 227/19 |
| 4,788,978 | 12/1988 | Strekopytov et al. . |
| 4,848,637 | 7/1989 | Pruitt . |
| 4,869,414 | 9/1989 | Green et al. . |
| 4,930,503 | 6/1990 | Pruitt . |
| 4,938,408 | 7/1990 | Bedi et al. . |
| 4,941,623 | 7/1990 | Pruitt . |
| 4,964,559 | 10/1990 | Deniega et al. . |
| 4,978,049 | 12/1990 | Green . |
| 4,994,065 | 2/1991 | Gibbs et al. . |
| 5,018,657 | 5/1991 | Pedlick et al. . |
| 5,027,834 | 7/1991 | Pruitt . |
| 5,100,042 | 3/1992 | Gravener et al. . |
| 5,137,198 | 8/1992 | Nobis et al. . |
| 5,190,203 | 3/1993 | Rodak . |
| 5,240,163 | 8/1993 | Stein et al. . |

FOREIGN PATENT DOCUMENTS

| | | |
|---|---|---|
| 0157888 | 3/1984 | European Pat. Off. . |
| 0136950 | 4/1985 | European Pat. Off. . |
| 0220029 | 4/1987 | European Pat. Off. . |
| 0273468 | 7/1988 | European Pat. Off. . |
| 2542188 | 3/1983 | France . |
| 1835500 | 4/1961 | Germany . |
| 1555455 | 11/1979 | United Kingdom . |
| 2141066 | 12/1984 | United Kingdom . |

*Primary Examiner*—Scott A. Smith

[57] ABSTRACT

A surgical stapling or fastening instrument for applying surgical fasteners to tissue having an adjustable closure mechanism to linearly approximate the distance between the jaw members of the instrument. The adjustable closure mechanism consists of a retaining mechanism and a linkage structure which is actuable to linearly urge the jaw members towards each other. A coupling arrangement is also provided which permits firing of the staples or fasteners only when the jaw members are approximated a predetermined distance towards each other.

39 Claims, 16 Drawing Sheets

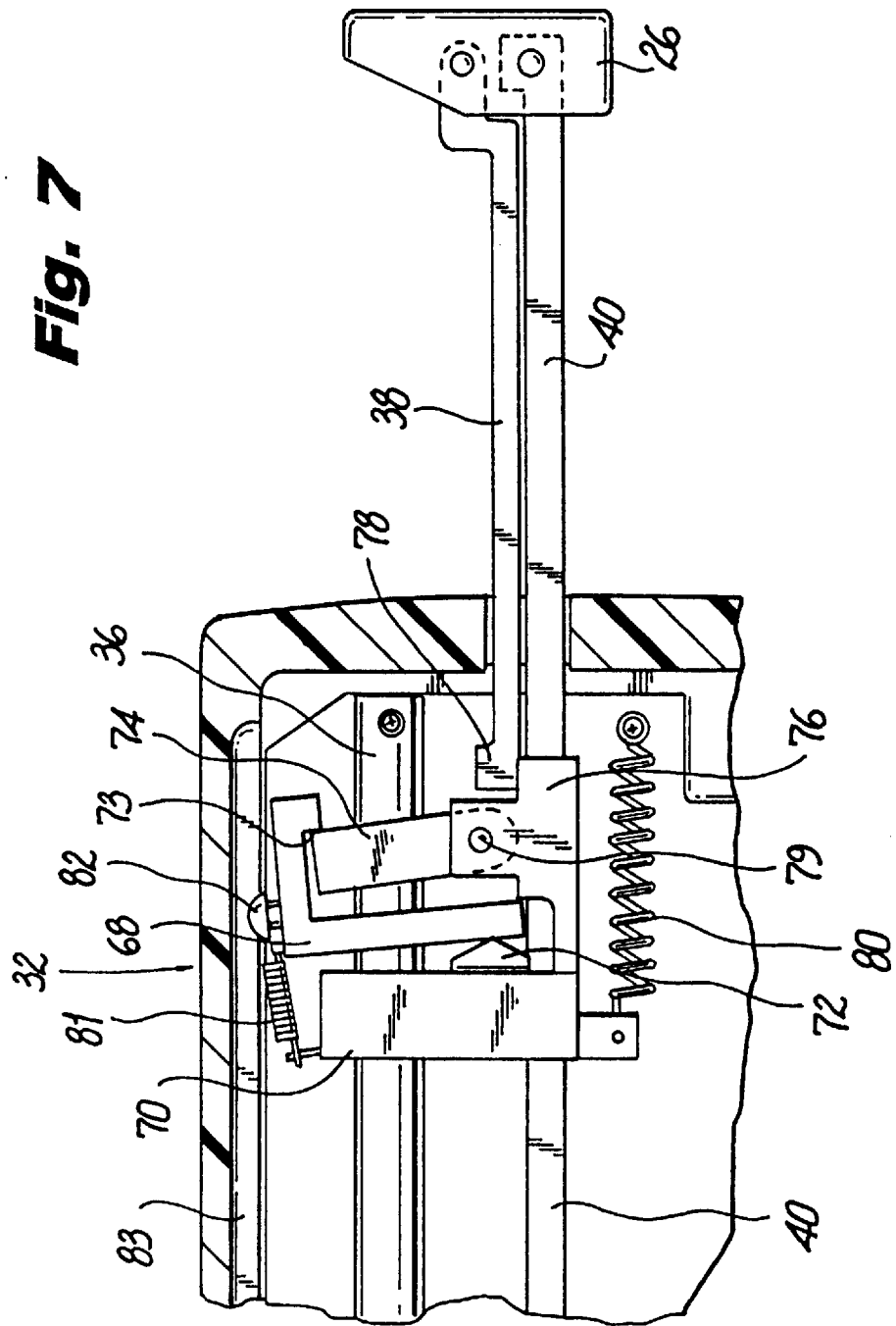

APPARATUS FOR APPLYING SURGICAL FASTENERS

This is a continuation of application Ser. No. 08/470,818 filed on Jun. 6, 1995, now abandoned, which is a division of Ser. No. 08/234,712 filed on Apr. 28, 1994, now U.S. Pat. No. 5,558,566, which is a continuation of Ser. No. 07/779,505 filed on Oct. 18, 1991 now abandoned.

BACKGROUND OF THE INVENTION

1. Field of the Invention

The present invention relates to surgical instruments for applying surgical fasteners or staples to body tissue, and more particularly to an apparatus for applying surgical fasteners having adjustable mechanisms for controlling the spacing between the jaw members through which the tissue passes during the fastening or stapling procedures.

2. Discussion of the Related Art

Surgical fastening devices having means for controlling the spacing between the jaw members are well known in the art. These devices typically include indicating means to provide a reading of the spacing between the jaw members. Devices are also known in the art which provide latching mechanisms to actuate the firing mechanism only when the distance between the jaws is within a preset range. These devices typically include a complex lock-out mechanism.

Various closing mechanisms are provided in the prior art for use with surgical fastening devices. The most notable of these devices utilize a complex worm gear-type arrangement or screw bearing member to open and close the spacing between the jaw members of the surgical fastening apparatus. These devices generally provide a rotatable knob or wing-like assembly at the trigger end of the device remote from the jaw mechanism which carries the fastener cartridge, and a screw-like mechanism is provided that passes through the body of the device to translate the rotational movement of the knob into longitudinal movement of the cartridge frame to open and close the spacing between the jaws. As the jaw members are closed around a tissue site to which fasteners are to be applied, the surgeon must grasp the device with one hand while rotating the knob or wing-like assembly with the other hand. As the jaws members close about the tissue to pinch the tissue therebetween, the surgeon then ceases rotation and activates the trigger mechanism to drive the fasteners into the tissue. Several known devices provide a trigger-like mechanism, while others provide a secondary rotatable knob for driving the fasteners by rotational movement. Many devices provide an indicator means near the rotatable knob which gives a visual indication of the spacing between the jaw members prior to firing.

These prior art devices are subject to several disadvantages in both use and construction which render these devices difficult to operate and expensive to manufacture. Many of the devices are cumbersome in use in that the surgeon must operate the device with both hands, holding the body of the instrument in one hand while rotating the knob or wing assembly with the other hand. This may lead to inaccurate stapling or fastening since the surgeon is unable to guide the tissue to be stapled or fastened with his free hand while closing the jaws about the tissue. Furthermore, the number of interacting components provides inaccuracies due to normal break down of tolerances. In addition, the gear arrangement may become worn during extended use, thus rendering an imprecise grasping action at the jaws.

Furthermore, these prior art devices generally involve a complex construction in which a precisely machined or cast worm gear must be constructed and incorporated into the device. This of course increases the cost of manufacturing, and requires a sophisticated assembly procedure to properly locate the worm gear in the instrument to control the spacing between the jaws.

Typical devices having a rotatable knob at the end portion adjacent the handle mechanism of the surgical stapling or fastening device are disclosed in, among others, U.S. Pat. No. 4,930,503 to Pruitt, U.S. Pat. No. 4,788,978 to Strekopytov et al., and U.S. Pat. No. 4,606,344 to DiGiovanni. In each of these devices, an elongated rod member having screw threads machined thereon is provided, which connects a rotatable knob positioned adjacent the handle members to a pusher mechanism which urges a movable jaw in a forward direction toward a stationary jaw to close the spacing between the jaw members. When a desired spacing is reached, a trigger mechanism may be activated to fire the fasteners through the tissue into the anvil member mounted on the stationary jaw. To remove the fastening instrument after application of the fasteners, the knob is rotated in an opposite direction which turns the screw threaded rod member to move the movable jaw member away from the stationary jaw member so that the entire device maybe removed from the tissue.

Surgical fastening instruments having a wing like arrangement positioned adjacent the handle assembly of a device for moving a movable jaw toward a stationary jaws for affixing surgical fasteners to tissue are disclosed in U.S. Pat. No. 4,442,964 to Becht, U.S. Pat. No. 4,354,628 to Green, and U.S. Pat. No. 3,795,034 to Strekopytov et al. These devices are similar to those described above except for the provision of a rotatable wing member in place of the rotatable knob. These devices are also provided with a screw threaded rod member which, when rotated, urges a movable jaw towards a stationary jaw to close the jaw members around tissue to be fastened together. After the application of surgical fasteners, the wing assembly is rotated in an opposite direction to draw the movable jaw away from the stationary jaw so that the instrument maybe removed from the tissue.

Surgical stapling of fastening instruments having a pivotable mechanism external to the device for moving a movable jaw toward a stationary jaw prior to affixing surgical fasteners to tissue are disclosed in, among others, U.S. Pat. No. 3,269,630 to Fleischer, U.S. Pat. No. 4,530,453 to Green, U.S. Pat. No. 4,715,520 to Roehr, Jr. et al., and U.S. Pat. No. 4,978,049 to Green.

Green ('453), Roehr, Jr. et al. and Green ('049) each disclose a pivotable lever member which urges a movable jaw into proximity of a stationary jaw prior to application of the surgical fasteners. Fleischer discloses a surgical stapling instrument in which a pivotable handle urges the movable staple cartridge against the tissue in the direction of the stationary jaw and fires the staples in the same motion. In each of these devices, removal of the instrument after firing of the surgical fasteners is accomplished by pivoting the lever mechanism in the opposite direction to open the jaw members by moving the movable jaw away from the stationary jaw.

Pending U.S. patent application Ser. No. 593,697 filed Oct. 5, 1990, discloses a spring biased pivotal catch member for approximating the jaws which is held in selected position by a pointed lance member.

The novel surgical stapling or surgical fastening device of the present invention obviates the disadvantages encountered in the prior art and provides an efficient surgical fastening device having an adjustable closure mechanism for controlling the spacing between the jaw members of the surgical fastening apparatus. The device of the present invention allows a surgeon to operate a surgical fastener with one hand while freeing the other hand to assist in the surgical procedure. Furthermore, the present invention provides a novel means for coupling the fastener driving mechanism to the firing mechanism when the jaws are approximated to a preset distance. The device of the present invention is of lightweight construction and provides ease of handling through the provision of a thumb controlled adjustable closure mechanism which permits a surgeon to set the spacing between the jaw members and fire the device while using only one hand.

SUMMARY OF THE INVENTION

The present invention provides a surgical fastening device having a novel mechanism for adjusting the distance between the movable jaw and the stationary jaw prior to the application of fasteners to the body tissue. The adjustable mechanism controls the closing of the jaw mechanism to approximate the distance between the jaw members prior to activation of the trigger mechanism to fire the fasteners. The device of the present invention may be operated with one hand, which frees the surgeon to accurately locate the tissue to be repaired and to place the fasteners in the proper position during the procedure. The adjustable closure mechanism is operable by using the thumb of the hand which holds the device, and linearly moves the stapling mechanism to properly approximate the distance between the jaw members. The adjustable closure mechanism of the present invention eliminates many moving parts associated with prior devices, and provides a device which is lightweight, and easy to use by allowing the surgeon to set and release the device with one hand.

The adjustable closure mechanism of the present invention may be used with any surgical instrument having jaw members which include a stationary jaw and a movable jaw, or two movable jaws, in which the spacing between the jaw members is adjustable to accommodate various thicknesses of tissue to be secured. The provision of the push button at the handle end of the instrument and the elimination of numerous complex moving parts which are common in prior art devices allows the surgeon to approximate the distance between the jaw members in a fast and efficient manner to position the jaws in the proper alignment for the application of surgical fasteners.

The apparatus of the present invention comprises a first jaw member and a second jaw member in which the first jaw member includes a plurality of fasteners positioned in a cartridge which is movable with the first jaw member towards the stationary second jaw member. The second jaw member may include an anvil surface for clinching the fasteners, or may include means for engaging the fasteners to secured the tissue therebetween. Means for advancing the first jaw member towards the second jaw member to grip the tissue between the jaws are provided, as well as releasable means for retaining the advancing means along a linear path of travel to selectively position the first jaw member in relation to the second jaw member. Means for driving the fasteners into the tissue subsequent to positioning the jaws members in relation to each other by the advancement means is also provided, and the advancement means of the apparatus of the present invention is independent of the driving means.

In a preferred embodiment a push button mechanism is provided at the handle end of the device which may be linearly displaced by the thumb of the surgeon. As the push button and slider bar arrangement is urged forwardly towards the jaws, the releasable retaining means is also urged forwardly within the housing of the apparatus to selectively position the jaws members in relation to each other. As the slider bar and releasable retaining means are continuously moved forward, a linkage arrangement is activated which urges the cartridge frame forward so that the cartridge moves towards the anvil. When the linkage arrangement is fully actuated, the proper distance between the jaw members is set, so that the trigger mechanism may be actuated to drive the fasteners through the tissues.

Preferably, a coupling mechanism is provided which couples the fastener driving means to the trigger mechanism to allow for driving of the staples or fasteners when the proper distance between the jaw members is set. As the slider mechanism is moved forward and the linkage arrangement actuated, the fastener driving means is urged forwardly with the cartridge frame. A coupling arm, which is connected at one end to the trigger mechanism, slides along a bearing surface on the driving means until the slider mechanism is fully deployed. At this point, a camming edge of the coupling arm engages a notch in the bearing surface of the driving means to couple the trigger mechanism to the driving means. At this point, the proper distance between the jaw members is set and the fastener means may be driven into the tissue.

After the fastening means have been driven into the tissue, the releasable retaining mechanism may be disengaged so that the jaw members may be returned to their original position whereby the fastening device may be removed from the surgical site. In the preferred embodiment, the push button is pivotable to move a second rod member which contacts a release lever which disengages the retaining means. In a second embodiment, a release knob is provided which extends through the housing of the fastening apparatus and which may be pivoted to release the retaining means.

BRIEF DESCRIPTION OF THE DRAWINGS

The foregoing features of the present invention will become more readily apparent and may be understood by referring to the following detailed description of an illustrative embodiment of the surgical fastening instrument and its novel adjustable closure mechanism, taken in conjunction with the accompanying drawings, in which:

FIG. 7 illustrates the retaining means of the present invention at the handle end of the device of FIG. 2 in the at rest condition;

DETAILED DESCRIPTION OF THE PREFERRED EMBODIMENTS

Figure 1:
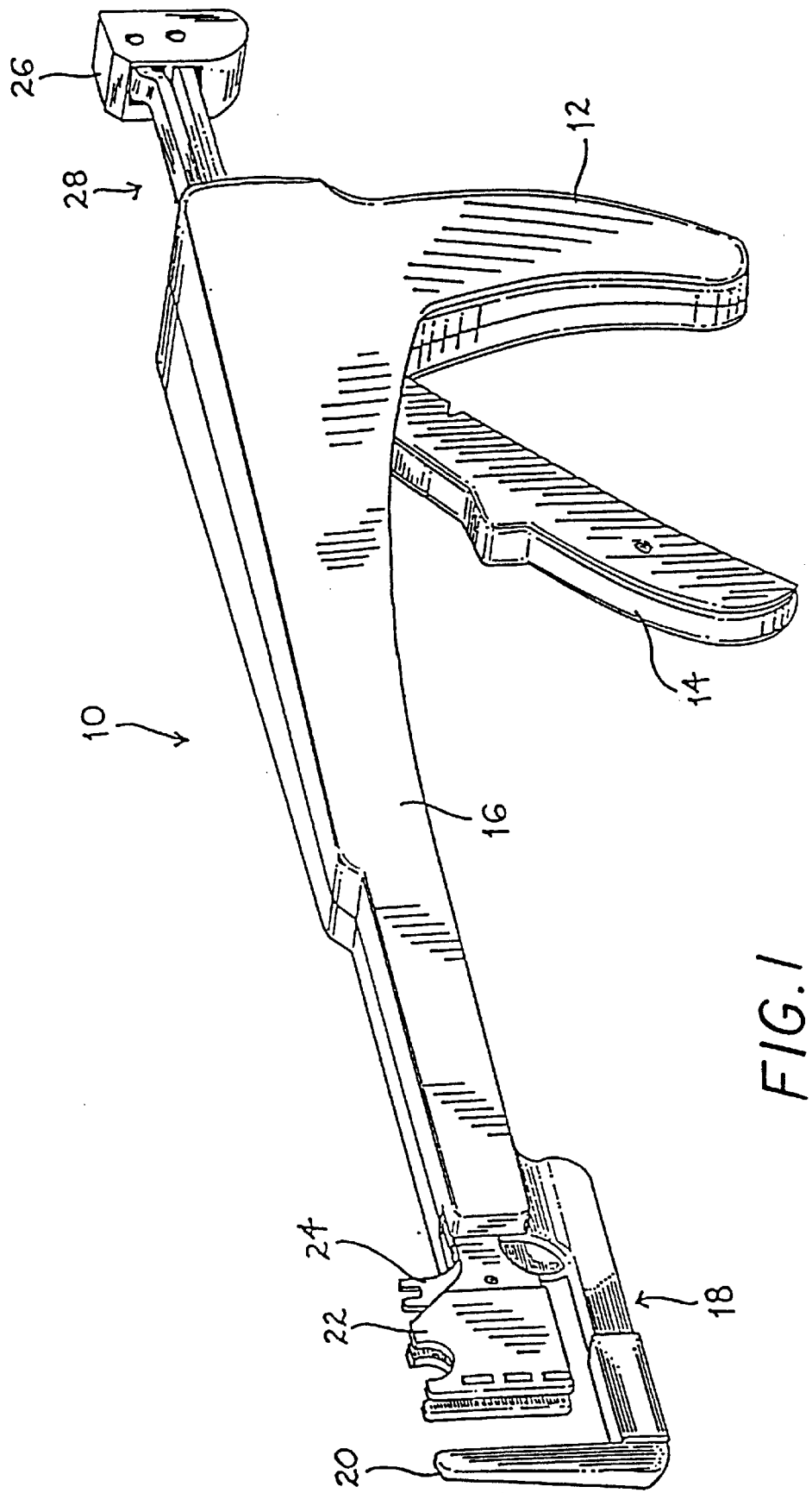
FIG. 1 illustrates a perspective view of a surgical fastening instrument employing the adjustable closure mechanism of the present invention.

Referring now in specific detail to the drawings, in which like reference numerals identify similar or identical elements throughout the several views, FIG. 1 shows a surgical fastening instrument 10 which employs the adjustable closure mechanism of the present invention. Fastening instrument 10 is provided with a housing configured to define a stationary handle 12 and an elongated body portion 16. The stationary handle 12 and an actuating handle 14 together comprise the trigger mechanism of instrument 10. The elongated body portion 16 terminates in a distal jaw mechanism 18 which includes an anvil jaw 20 and a cartridge jaw 22. A fastening cartridge (not shown) is positioned within cartridge jaw 22 for driving staples or fasteners through tissue against an anvil surface positioned on anvil jaw 20. Alternatively, the cartridge can contain the fastener portions of two part fasteners which are driven into retainers positioned on the anvil jaw. At the handle end of instrument 10 is provided a push button 26 for operating an advancement mechanism 28, whose function will be described below.

Figure 2:
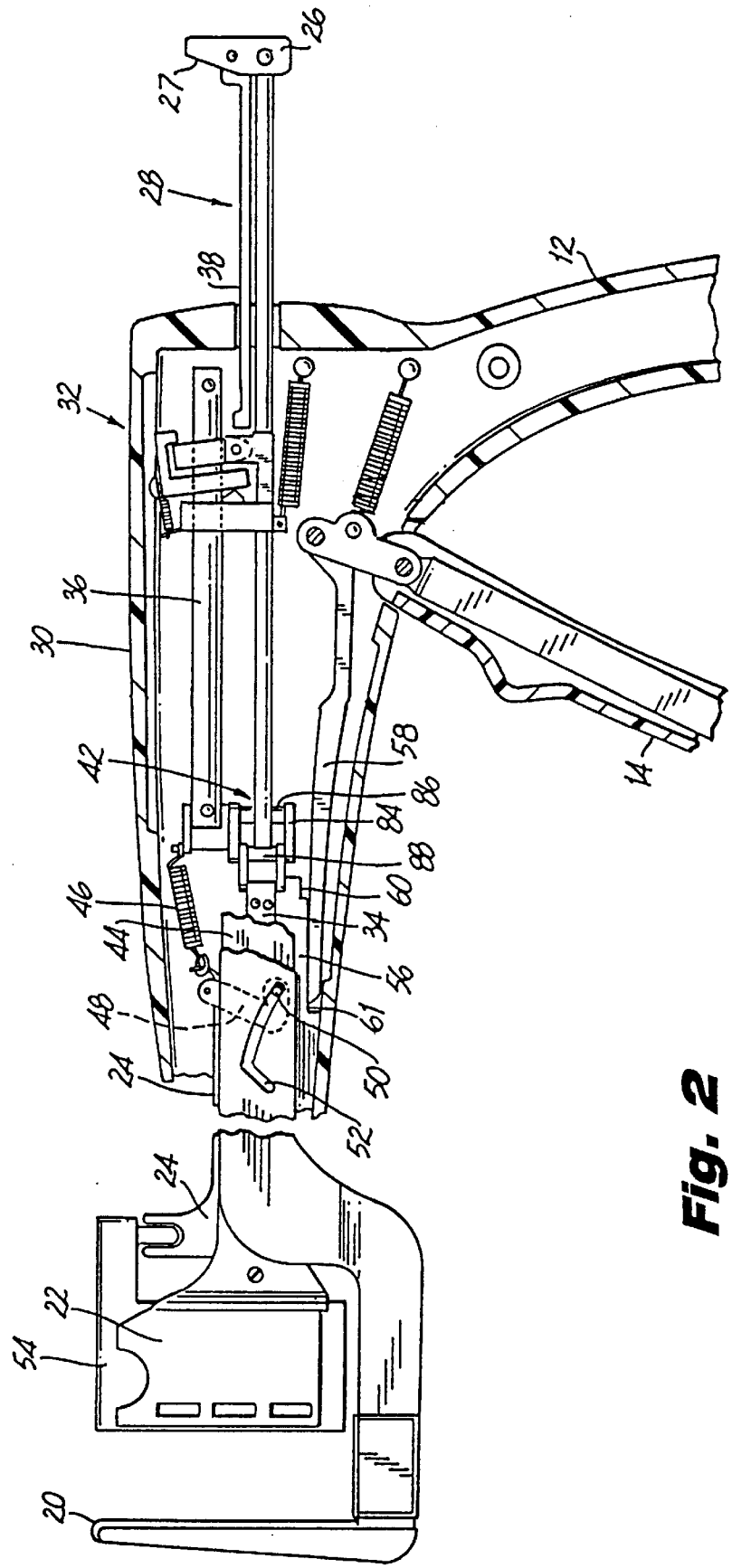
FIG. 2 illustrates a side cross-sectional plan view of a surgical fastening instrument employing the adjustable closure mechanism of the present invention in which the instrument is in an at rest condition.

As seen in FIG. 2, push button 26 and advancing mechanism 28 extend outwardly from the handle end of the instrument 10 through the housing. A releasable retaining mechanism 32 is slidably engaged to the stationary rod member 36 and is coupled to slider mechanism 40 so that as slider mechanism 40 is urged forwardly into housing 30, retaining mechanism 32 is slidably retained along stationary rod member 36.

Advancing mechanism 28 comprises slider mechanism 40. The slider mechanism includes an elongated member having a proximal end connected to a release rod member 38 by a push button 26. Thrusting push button 26 towards housing 30 slides release rod 38 and slider mechanism 40 into the housing to move the retaining mechanism 32 along rod 36. Slider mechanism 40 extends to linkage structure 42 to activate the linkage structure 42 and urge jaw mechanism 18 distally. Linkage structure 42 moves movable rod 34, as well as fastener driver 56, cartridge frame 44, alignment pin advancement means 24, and cartridge 54 all in a distal direction to selectively position movable cartridge jaw 22 and stationary anvil jaw 20.

For purposes of clarity, the individual mechanisms will be described separately, and then the overall operation of the device will be discussed.

Figure 7A:
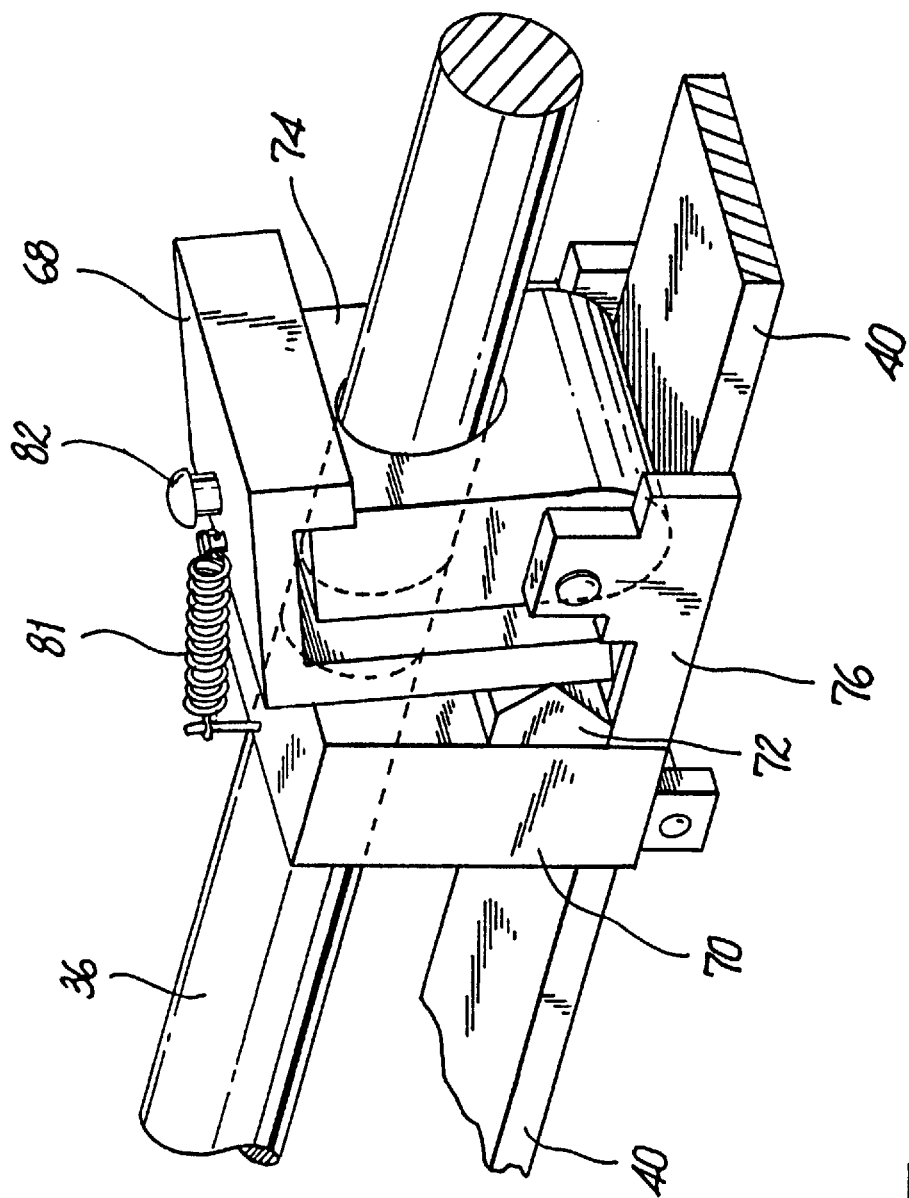
FIG. 7a illustrates a perspective view of the retaining mechanism of FIG. 7.
Figure 15B:
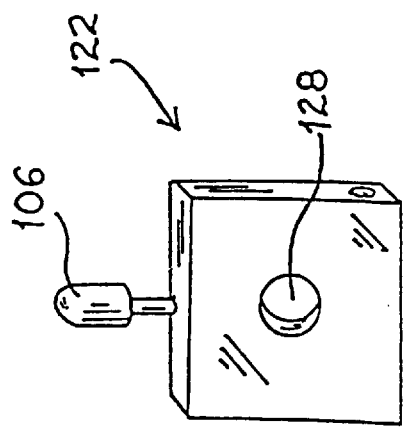
FIGS. 15A and 15B illustrate embodiments of the retaining means of the adjustable closure mechanism of the present invention.
Figure 15A:
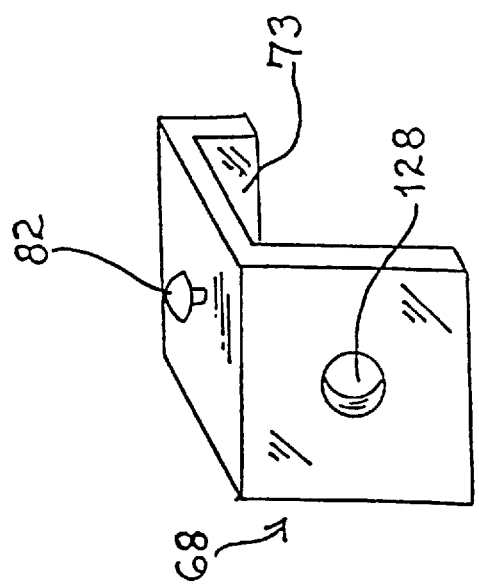

FIGS. 7 and 7A illustrate a retaining mechanism of the present invention, which slidably engages the stationary rod 36, and which acts in conjunction with the linkage structure 42 to selectively position the jaw mechanism 18 of the surgical fastener apparatus 10. Retaining mechanism 32 is coupled to slider mechanism 40 and is urged rearwardly by biasing spring 80 as shown. The retaining mechanism 32 essentially comprises a clamp member 68 and a block member 70. The clamp member 68 is provided with a central bore 128 through which stationary rod 36 passes. Clamp member 68 is best seen in FIG. 15A. The block member 70 to is pivotally secured to the clamp member 68 and biased into a locking engagement of stationary rod 36 by spring member 81. Spring member 81 may comprise a coiled spring as shown, or may further comprise any other biasing mechanism such as a leaf spring, rubber block, or the like. Block member 70 may be provided with a central bore (not shown) through which stationary rod 36 passes, or alternatively, block member 70 may have a substantially U-shaped portion to allow stationary rod 36 to pass therethrough. Block member 70 further comprises shoulder portion 72 which abuts the lower portion of clamp member 68 as shown to provide a pivot point for releasing clamp member 68, as will be described below.

As best seen in FIG. 15A, clamp member 68 has an L-shaped portion terminating in a contact face 73 which engages a release mechanism including a release lever 74, which is pivotably connected to carriage 76 and which pivots about pivot point 79. Carriage 76 is secured to the slider mechanism 40. Release lever 74 preferably has a central bore to allow the stationary rod 36 to pass therethrough, but may also be provided with a U-shaped body both to surround stationary rod 36 and engage contact face 73 of clamp member 68. Clamp member 68 is further provided with a guide post 82 which slides within a guide track 83 to fully align clamp member 68 in relation to stationary rod 36.

Figure 6:
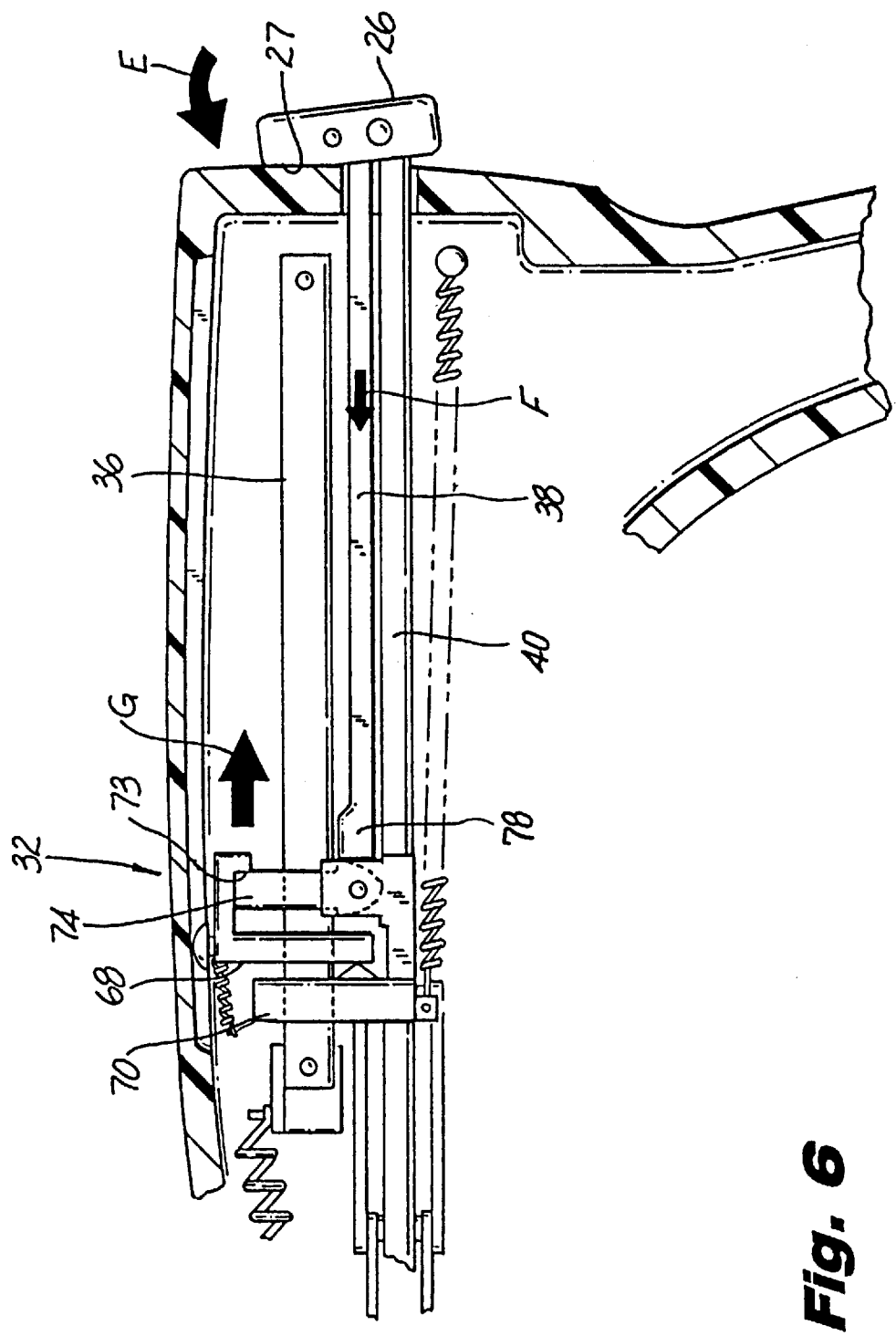
FIG. 6 illustrates a partial enlarged view of the handle end of the device of FIG. 2 showing the release mechanism for disengaging the retaining means of the present invention.

As shown in FIG. 7, clamp member 68 is biased at an angle to engage stationary rod 36 so that edges of central bore 128 frictionally engage stationary rod member 36. As push button 26 is urged towards housing 30, retaining mechanism 32 slides along stationary rod 36 due to the movement of advancing mechanism 28. Carriage 76 is engaged with movable slider mechanism 40 so that the entire retaining mechanism is urged distally against biasing spring 80. In order to release retaining mechanism 32, as best shown in FIG. 6, a release mechanism including release rod 38 and release lever 74 is actuated by rotating push button 26 in the direction of arrow E until beveled surface 27 contacts housing 30. Pivoting push button 26 in the direction of arrow E actuates the release mechanism by moving the release rod 38 in the direction of arrow F so that contact surface 78 of release rod 38 pivots release lever 74 to engage contact face 73 of clamp member 68. This pivoting action moves clamp member 68 in the direction of arrow G to release the frictional engagement of the central bore 128 with stationary rod 36. Releasing the frictional engagement causes the entire retaining mechanism 32 to return in the direction of arrow G to the position shown in FIG. 7. This movement is caused by biasing spring 80 (not shown in FIG. 6) which moves the entire mechanism to the position shown in FIG. 7.

Figure 8:
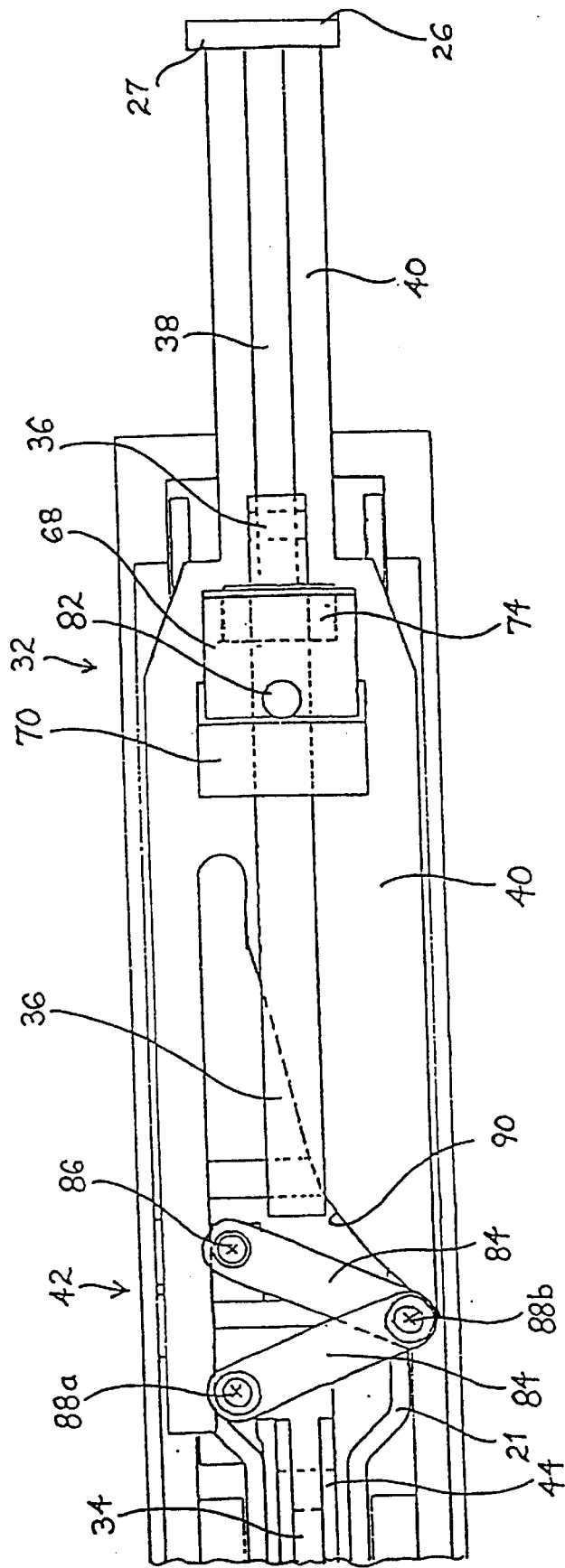
FIG. 8 illustrates a top plan cutaway view of the instrument of FIG. 1 showing the adjustable closure mechanism of the present invention in the at rest condition.
Figure 9:
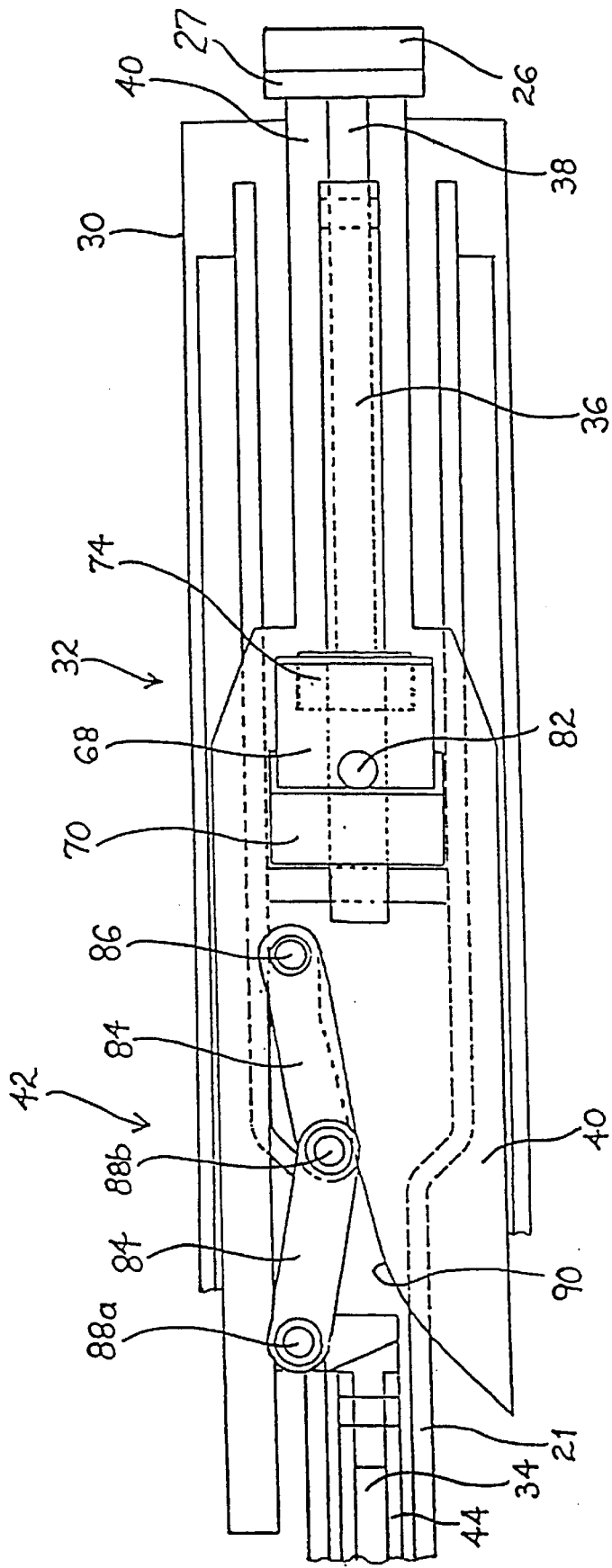
FIG. 9 shows a top plan cutaway view of the instrument of FIG. 1 showing the adjustable closure mechanism of the present invention in the fully deployed condition.

Turning now to FIGS. 8 and 9, there is illustrated the linkage structure 42 and its operation in conjunction with slider mechanism 40 and retaining mechanism 32. Structure 42 comprises a pair of linkage arms 84, which are preferably secured by pivot posts to a second pair of linkage arms 84 located below the pair shown in FIG. 8 in mirror arrangement, as clearly shown in FIGS. 2–6. Linkage arms 84 are joined through stationary pivot post 86, and movable pivot posts 88A and 88B. Movable pivot post 88A is secured to rod 34 and cartridge frame 44 to urge these elements distally when push button 26 is activated. Slider mechanism 40 includes a camming surface 90 which engages movable pivot post 88B to collapse linkage structure 42 to move the rod 34 and cartridge frame 44, and consequently move cartridge jaw 22 towards anvil jaw 20.

As best seen in FIG. 9, as push button 26 is fully actuated to contact housing 30, retaining mechanism 32, being coupled to slider mechanism 40 slides along stationary rod 36. Camming surface 90 engages movable post 88B, driving movable post 88A distally to move movable rod 34 and cartridge frame 44 in relation to housing frame 21 as shown. Releasing retaining mechanism 32 as described above returns linkage structure 42 to the configuration shown in FIG. 8.

It can be appreciated from FIGS. 8 and 9 that the linkage structure 42 provides a two-stage approximation of the jaw mechanism 18, whereby initial movement of the slider mechanism 40 caused a large initial approximation, while a smaller, secondary approximation eases the jaws into approximation at the conclusion of movement of the slider mechanism 40. As slider mechanism 40 is initially moved upon actuation of the push button 26, a large portion of the overall distance cartridge jaw member 22 travels towards anvil jaw member 20 is traversed in the initial movement. Typically, as the slider mechanism 40 travels approximately one-half its overall distance, and correspondingly moving movable pivot post 88A a portion of its total distance, cartridge jaw 22 moves approximately 80% of its total distance. As slider mechanism 40 travels its remaining one-half distance, the cartridge jaw moves its final 20% of its total distance. This allows for a fine adjustment of the jaw mechanism to accommodate the various thickness of tissues positioned between the jaw members.

Instrument 10 employing the novel adjustable closure mechanism of the present invention may further include a coupling device for coupling the fastener driving mechanism to the trigger mechanism only when a proper distance between cartridge jaw 22 and anvil jaw 20 has been reached. This mechanism is best illustrated in FIGS. 14A through 14C.

Figure 14A:
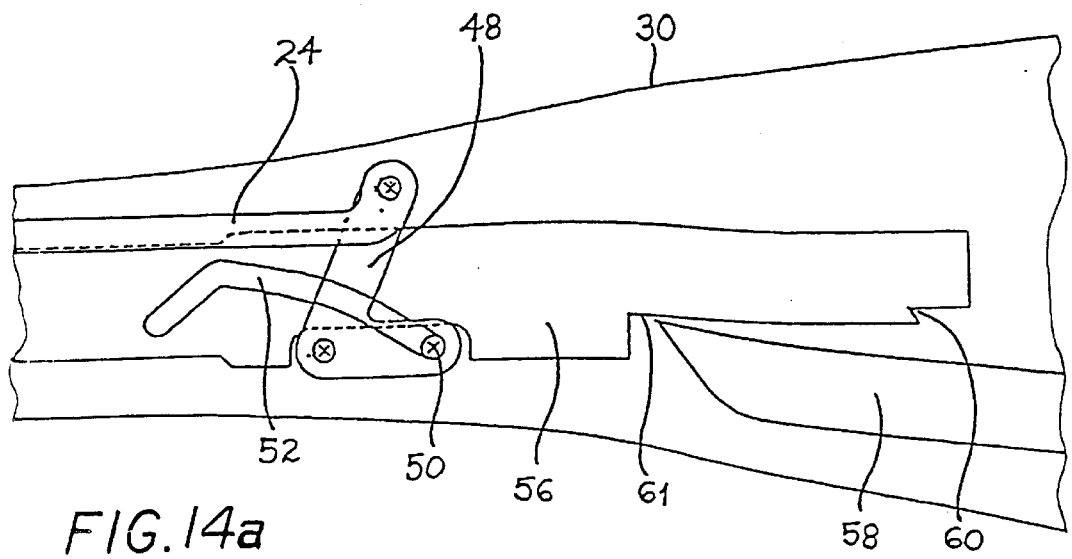
FIGS. 14A–14C illustrate the coupling mechanism according to the present invention for coupling the trigger mechanism to the fastener driving mechanism used in conjunction with the adjustable closure mechanism of the present invention.
Figure 14B:
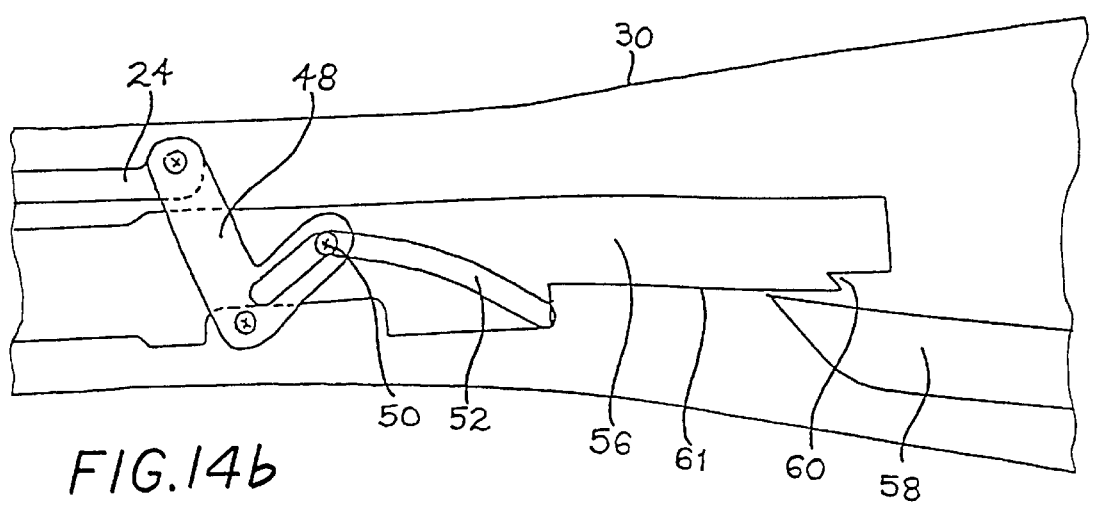
Figure 14C:
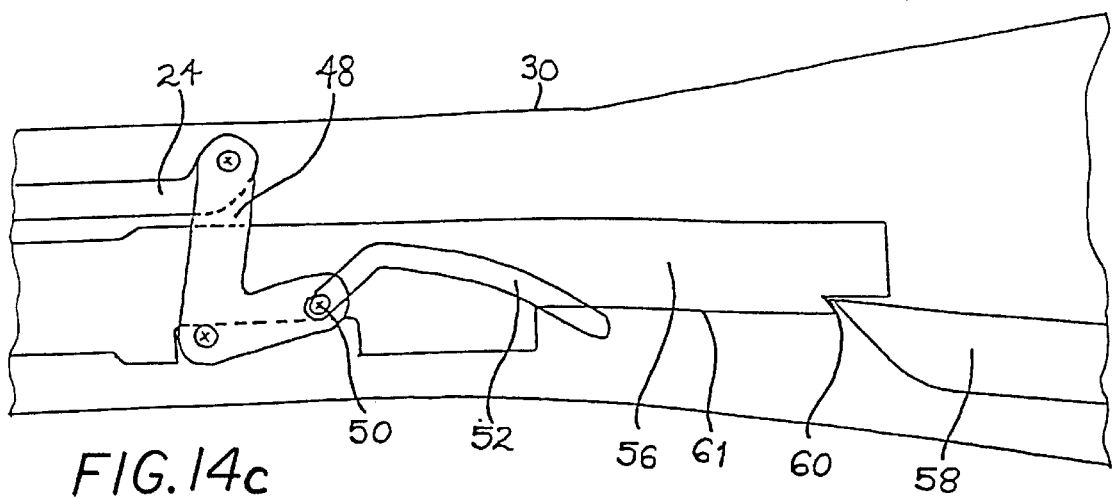

FIGS. 14A through 14C, in conjunction with FIGS. 2–6, illustrate the coupling mechanism of the present invention. Housing frame 21 is provided with a frame track 52 within which a driving pin 50 rides. Driving pin 50 is secured to one leg of an L-shaped driving link 48, where the opposite end of driving link 48 is secured to the alignment pin advancement means 24. Driving link 48 is further coupled to cartridge frame 22 which is advanced distally when push button 26 is actuated. As push button 26 is actuated, linkage structure 42 is deployed and fastener driver 56 is moved distally. Prior to actuation of push button 26, fastener driver 56 is in the position shown in FIG. 14A, and coupling arm 58 is positioned on bearing surface 61 as shown. Coupling arm 58 is connected to actuating handle 14 as best seem in FIG. 2.

Figure 3:
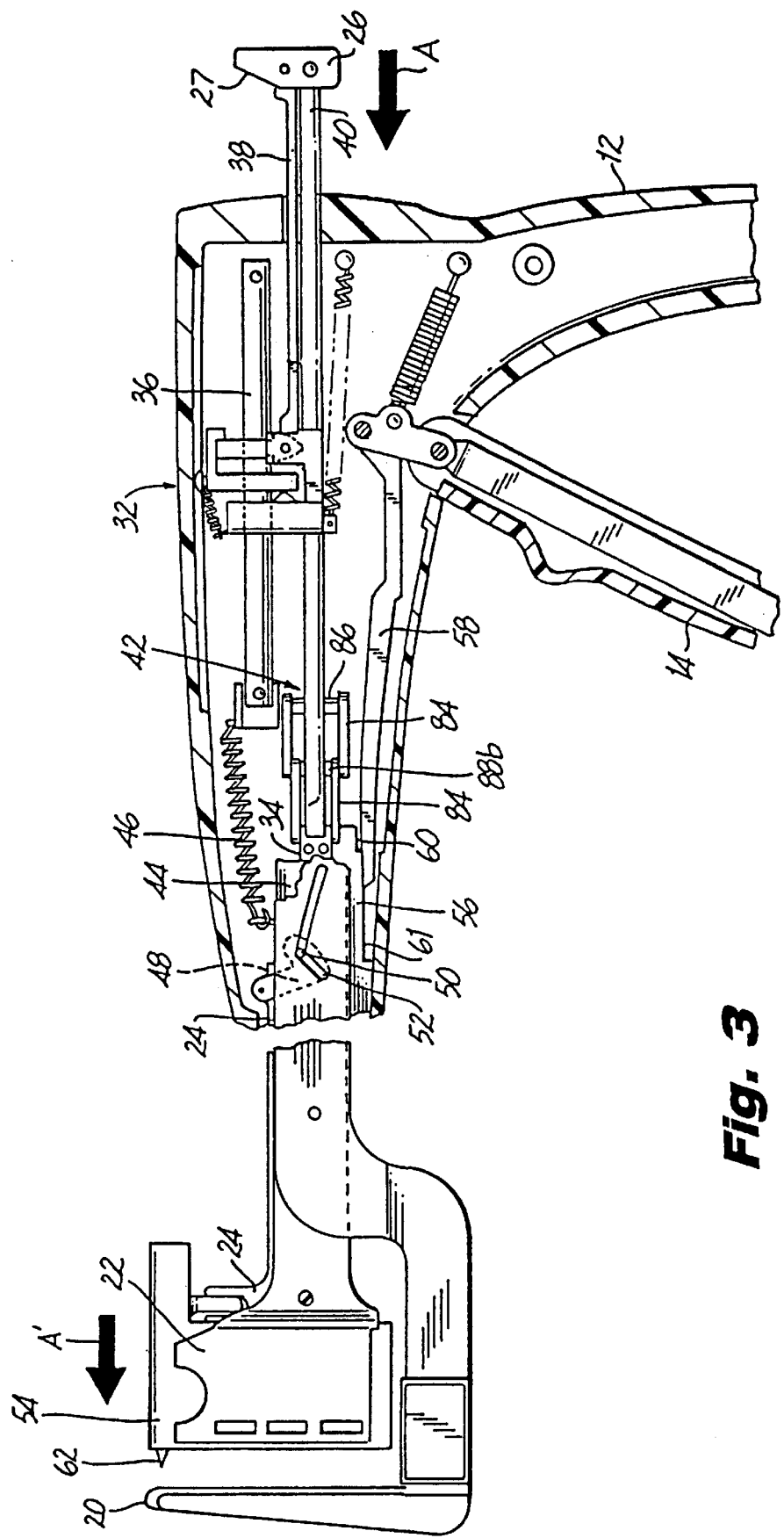
FIG. 3 illustrates the device of FIG. 2 in which the adjustable closure mechanism is activated and the jaw mechanism is partially closed.

As push button 26 is moved, fastener driver 56 is moved forwardly so that coupling arm 58 slides along bearing surface 61 as shown in FIG. 14B. Driving pin 50 travels in frame track 52, while driving link 48 urges alignment pin advancement means 24 as shown. As best seen in FIG. 3, alignment pin advancement means 24 moves forwardly so that alignment pin 62 protrudes from cartridge 54 and aligns with an alignment hole (not shown) in anvil jaw 20. This insures proper alignment of cartridge 54 with anvil jaw 20 so that fastener means 66 are properly driven into position between the jaw members.

Figure 4:
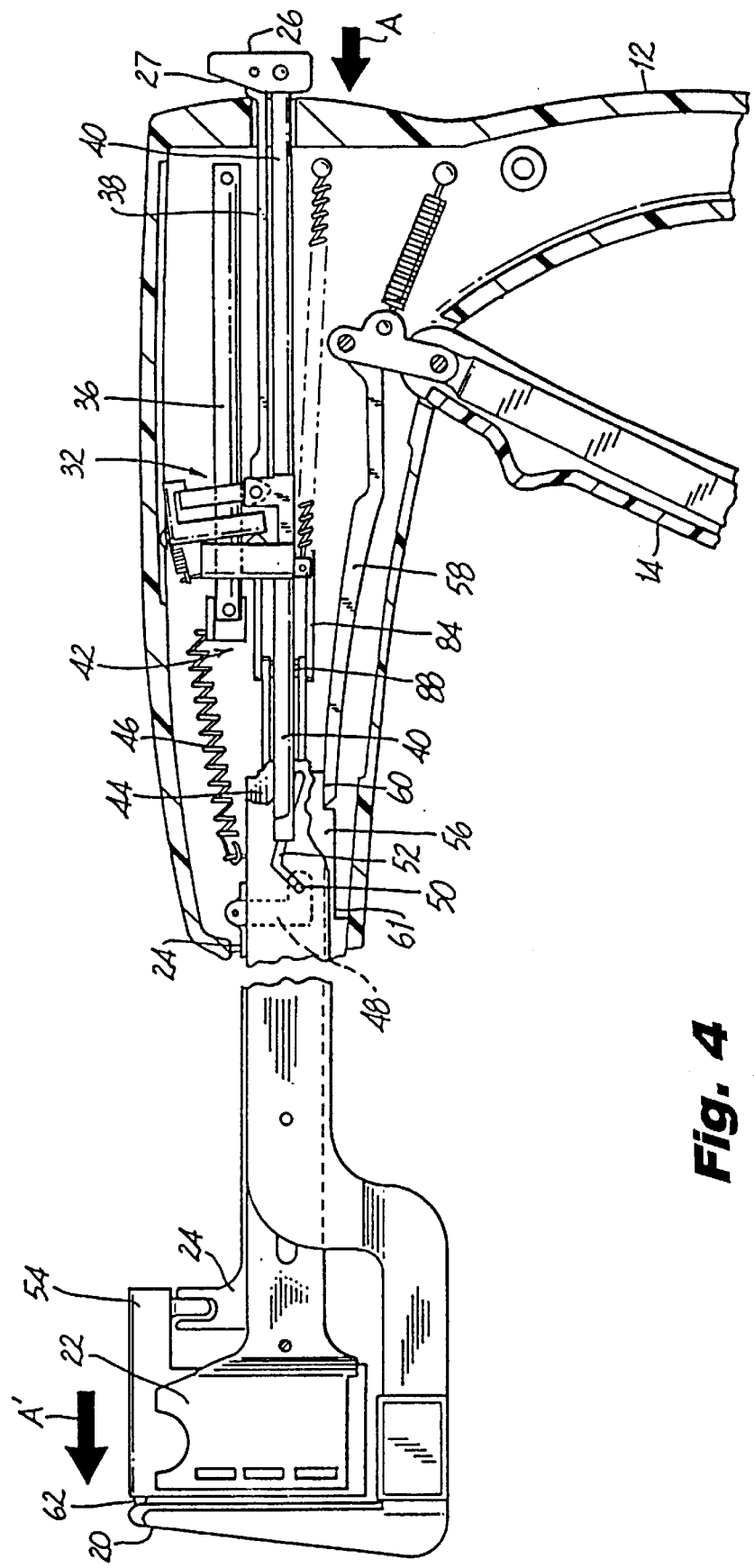
FIG. 4 illustrates the device of FIG. 2 in which the adjustable closure mechanism of the present invention is fully deployed.

As push button 26 is further moved towards housing 30, to the position shown in FIG. 4, cartridge jaw 22 is aligned adjacent anvil jaw 20 so that pin 62 is within the hole in anvil jaw 20. Driving link 48 moves slightly in the proximal direction towards the handle end of instrument 10 to a substantially upright position as shown in FIG. 14C and FIG. 4. This moves alignment pin advancement means 24 slightly proximally to the position shown in FIG. 4 so that alignment pin 62 does not protrude completely through anvil jaw 20.

Figure 5:
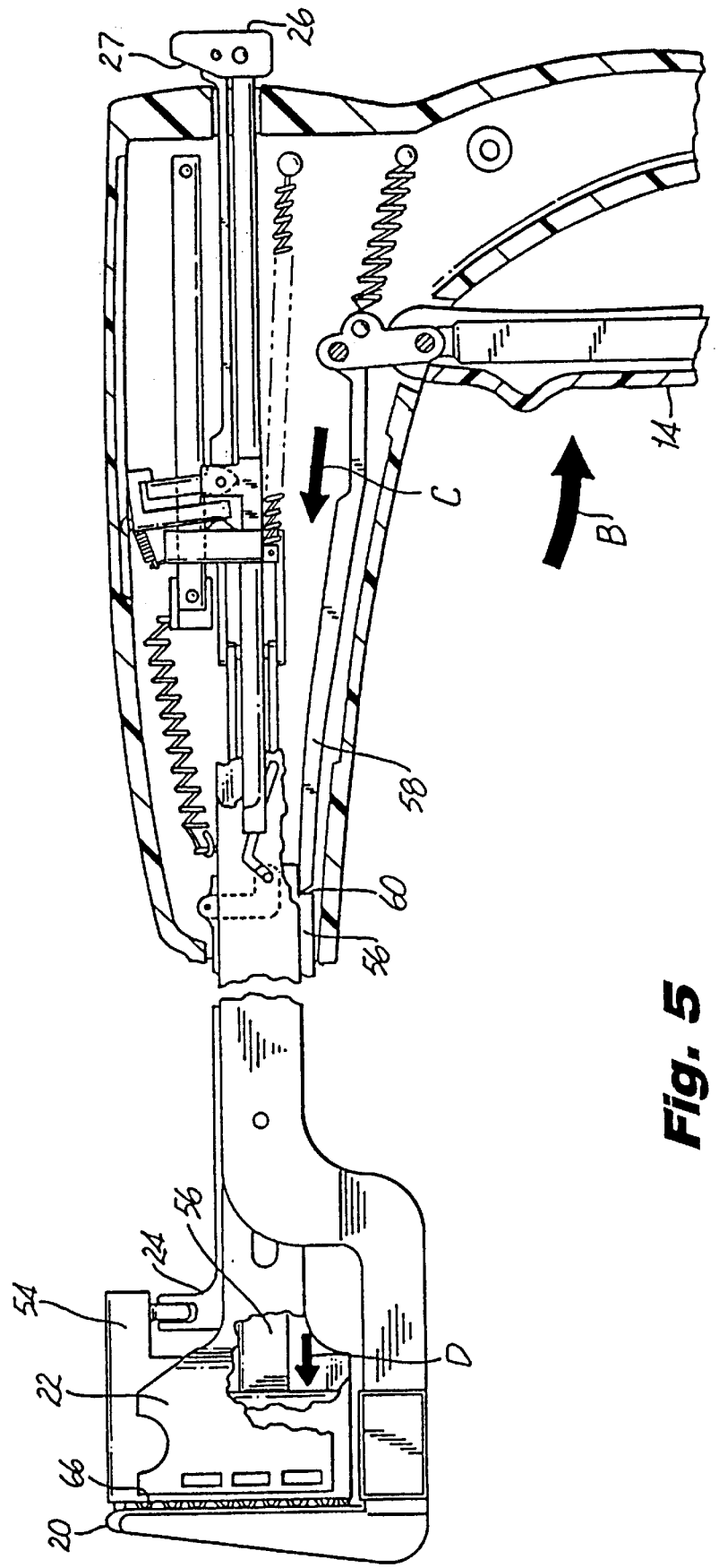
FIG. 5 illustrates the device of FIG. 2 in which the adjustable closure mechanism of the present invention is fully deployed and the trigger mechanism of the device has been actuated so that the fastening means have been driven from the cartridge.

When push button 26 reaches the position shown in FIG. 4, fastener driver 56 has moved distally to a position where coupling arm 58 slides off bearing surface 61 and into notch 60 as shown in FIG. 14C. At this point, driving link 48 has moved to the position shown in FIG. 14C and driving pin 50 has fully traversed the length of frame track 52. In the position shown in FIG. 14C, coupling arm 58 is engaged with fastener driver 56 so that actuation of handle 14 as shown in FIG. 5 will drive fastener means 66 into the tissue as fastener driver 56 moves in the direction of arrow D. Although not shown, coupling arm 58 may be provided with a leaf spring member to urge coupling arm 58 into engagement with notch 60. As push button 26 is rotated to release retaining mechanism 32, driving pin 50 travels proximally in frame track 52, so that when driving pin 50 reaches the position shown in 14B fastener driver 56 is lifted off coupling arm 58 despite the leaf spring, and coupling arm 58 is no longer engaged in notch 60. As retaining means 32 returns the entire mechanism to the position shown in FIG. 2, driving link 48 and fastener driver 56 return to the position shown in FIG. 14A.

Returning now to FIGS. 2 through 6, the operation of the surgical fastener apparatus 10 having the adjustable closure mechanism of the present invention will now be described.

After tissue which is to be surgically repaired is positioned between cartridge jaw 22 and anvil jaw 20, push button 26 is pushed in the direction of arrow A as seen in FIG. 3 which moves slider mechanism 40 and release rod 38 into housing 30. Retaining mechanism 32 is slid distally along stationary rod 36, and camming surface 90 of slider mechanism 40 engages stationary post 88B to deploy linkage structure 42. As linkage structure 42 is deployed, movable rod 34 is urged forwardly along with cartridge frame 44, thus urging driving pin 50 along frame track 52. The force of biasing spring 46 is overcome as push button 26 is urged in the direction of arrow A.

As driving pin 50 moves in track 52, driving link 48 is moved to the position shown in FIG. 3, which urges alignment pin advancement means 24 to the position shown at the jaw mechanism 18. In this position, alignment pin 62 protrudes from cartridge 54 and aligns with the alignment hole in anvil jaw 20 as cartridge 54 moves in the direction of arrow A'.

As linkage structure 42 is deployed and movable rod 34 and cartridge frame 44 move distally, fastener driver 56 also moves distally and coupling arm 58 slides along bearing surface 61.

When push button 26 is fully actuated, linkage structure 42 is fully deployed as shown in FIG. 4, and retaining mechanism 32 frictionally engages stationary rod 36 to maintain instrument 10 in the position shown in FIG. 4. At this time, cartridge 54 has moved into position in the direction of arrow A' so that alignment pin 62 is positioned in the alignment hole in anvil jaw 20. Alignment pin advancement means 24 moves slightly proximally so that alignment pin 62 does not protrude beyond anvil jaw 20, and driving link 48 assumes the position shown in FIG. 4. Driving pin 50 has reached the end of track 52. In the position shown in FIG. 4, actuating arm 58 has slid off bearing surface 61 and into notch 60 of fastener driver 56 so that the device as shown in FIG. 4 is ready to be fired. Once in the position of FIG. 4, actuating handle 14 is moved in the direction of arrow B to fire the fasteners 66. As actuating handle 14 is moved in the direction of arrow B against the force of biasing spring 64, coupling arm 58, having been engaged in notch 60, moves in the direction of arrow C to move fastener driver 56 distally in the direction of arrow D. Fastener driver 56 drives fasteners 66 from cartridge 54 through the tissue (not shown) and into the anvil surface of anvil jaw 20. Upon completion of firing, actuating handle 14 is released and returns to the position shown in FIG. 4.

To remove instrument 10 from the surgical site, it is necessary to release the jaw mechanism 18 to return to the position shown in FIG. 2. This is accomplished by pivoting push button 26 in the direction of arrow E, as best seen in FIG. 6, so that beveled surface 27 contacts the housing 30. As push button 26 is pivoted in the direction of arrow E, release rod 38 travels in the direction of arrow F so that contact surface 78 of release rod 38 pivots release lever 74 as shown, which engages contact face 73 to move clamp member 68 to an upright position and perpendicular in relation to stationary rod 36. This releases the frictional engagement of clamp member 68 with stationary rod 36 and the entire retaining mechanism 32 is moved along stationary rod 36 in the direction of arrow G due to the force of biasing spring 80 (as shown in FIG. 7). The entire mechanism, including the linkage structure 42, jaw mechanism 18, and retaining mechanism 32 is returned to the position shown in FIG. 2.

Figure 10:
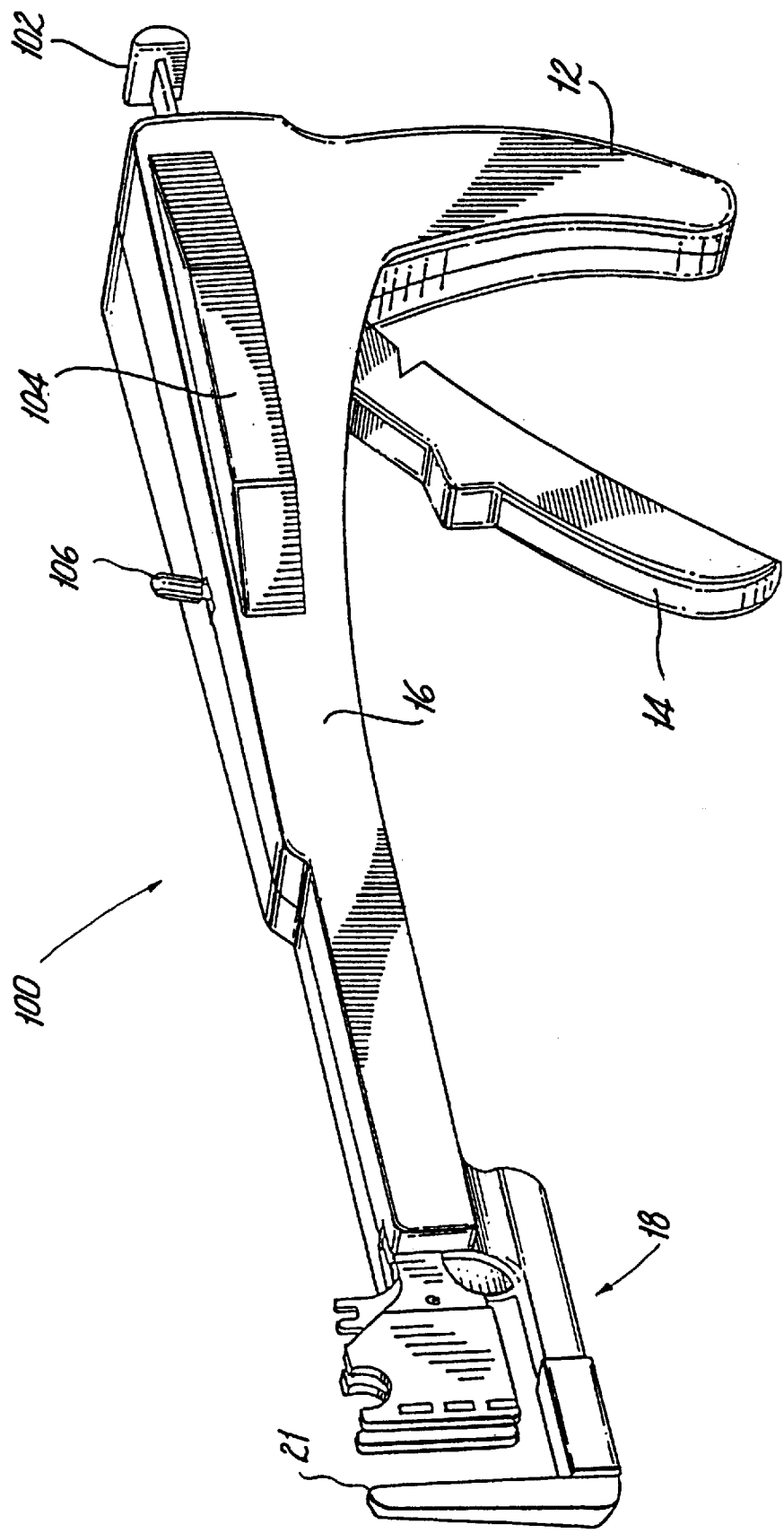
FIG. 10 illustrates a perspective view of the surgical fastening apparatus employing an alternative embodiment of the adjustable closure mechanism of the present invention.

FIG. 10 illustrates a surgical fastening apparatus 100 employing an alternative adjustable closure mechanism according to the present invention. Apparatus 10 is similar to apparatus 10 of FIG. 1 in that a stationary handle 12 and an actuating handle 14 are provided, along with a body portion 16 and a jaw mechanism 18. Body portion 16 is provided with a flared portion 104 which is symmetrical on both sides of the instrument for accommodating the slider mechanism which will be described below. A push button 102 is provided for actuating the slider mechanism, and a release button 106 is provided to release the retaining mechanism as will be described below.

Figure 11:
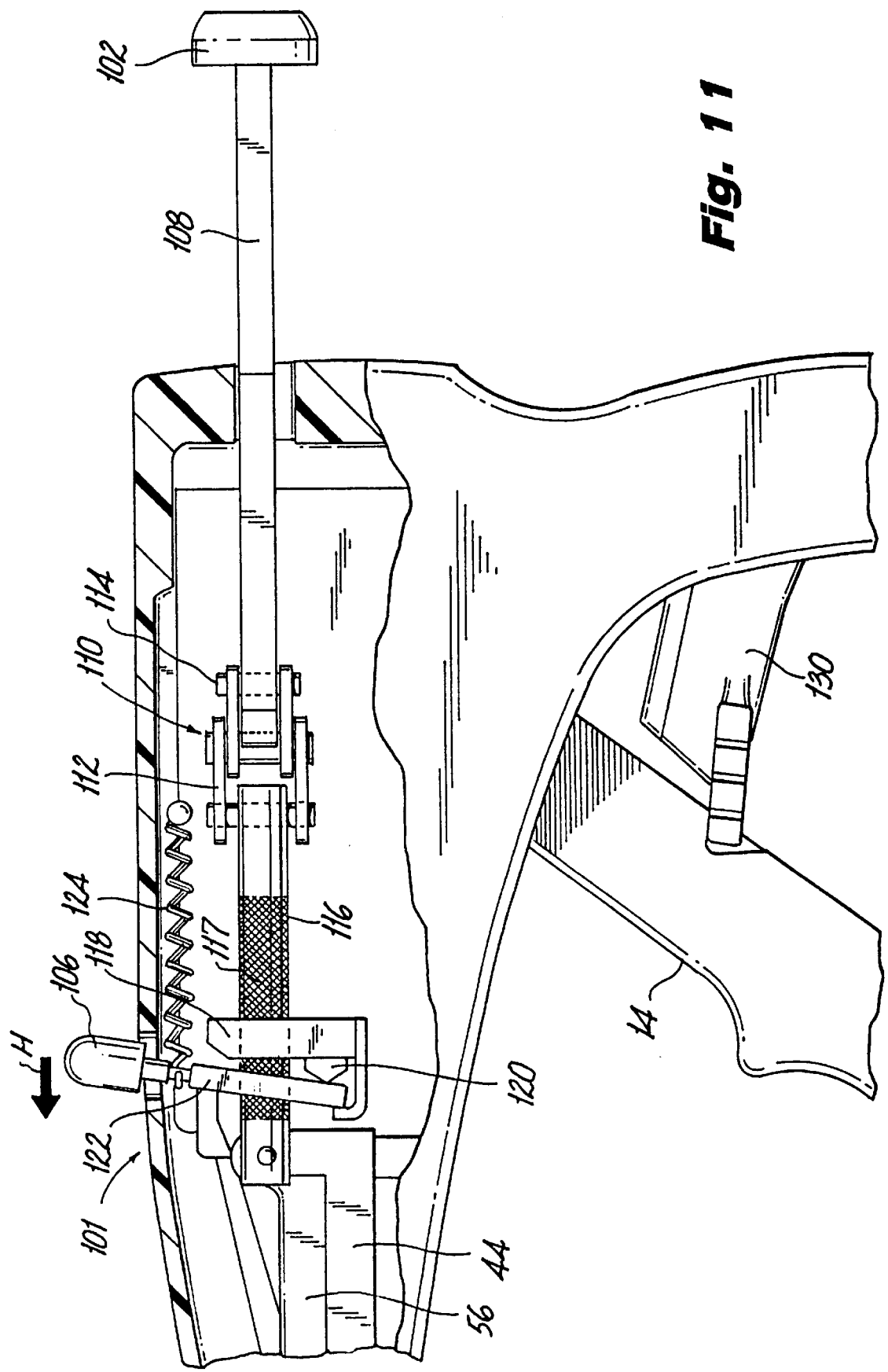
FIG. 11 illustrates a side cutaway view of the handle end of the instrument of FIG. 10 showing the adjustable closure mechanism of the present invention.

Turning now to FIG. 11, there is shown the adjustable closure mechanism of the apparatus of FIG. 10. Instrument 100 is substantially identical to instrument 10 except for retaining mechanism 101 and linkage structure 110.

Figure 12:
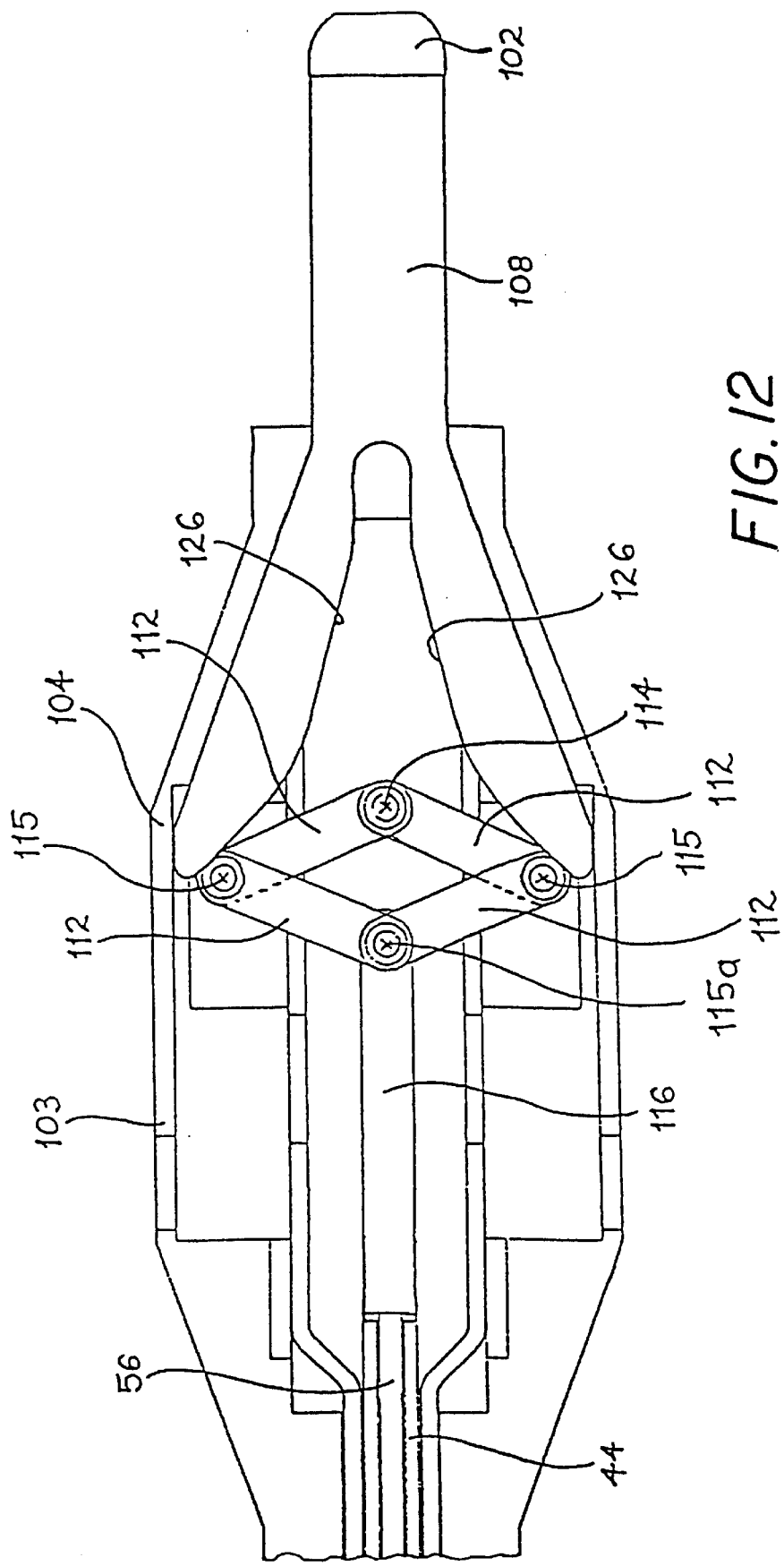
FIG. 12 illustrates a top plan cutaway view of the device of FIG. 10 showing the linkage arrangement of the adjustable closure mechanism of the present invention in an at rest condition.

Linkage structure 110 comprise a plurality of linkage arms 112, as best seen in FIG. 12. Linkage arms 112 form a collapsible box structure having a mirror image as shown in FIG. 11. Linkage arms 112 are joined by stationary pivot post 114 and movable pivot posts 115. As seen in FIG. 12, movable pivot post 115A is secured to movable rod 116 whose function will be described below. Push button 102 is connected to slider mechanism 108 which is provided with an essentially Y-shaped configuration. The outer ends of the Y-shaped slider mechanism are accommodated in flared portions 104 of the housing 103 of instrument 100. Movable rod 116 extends from movable pivot point 115A through retaining mechanism 101 to connect to fastener driver 56 and cartridge frame 44 as shown. Movable rod 116 is frictionally engaged by retaining mechanism 101 to selectively position cartridge jaw 22 in relation to anvil jaw 20.

Retaining mechanism 101 comprises clamp member 122 and block member 118 which is provided with shoulder 120. Clamp member 122, as best seem in FIG. 15B, is provided with a central bore 128 whose edges frictionally engage movable rod 116. Movable rod 116, as well as stationary rod 36 of the embodiment of FIGS. 1–9, may be provided with a scored surface to enhance the frictional gripping of clamp members 122 and 68. Clamp member 122 is biased into the engaged position by biasing spring 124.

Figure 13:
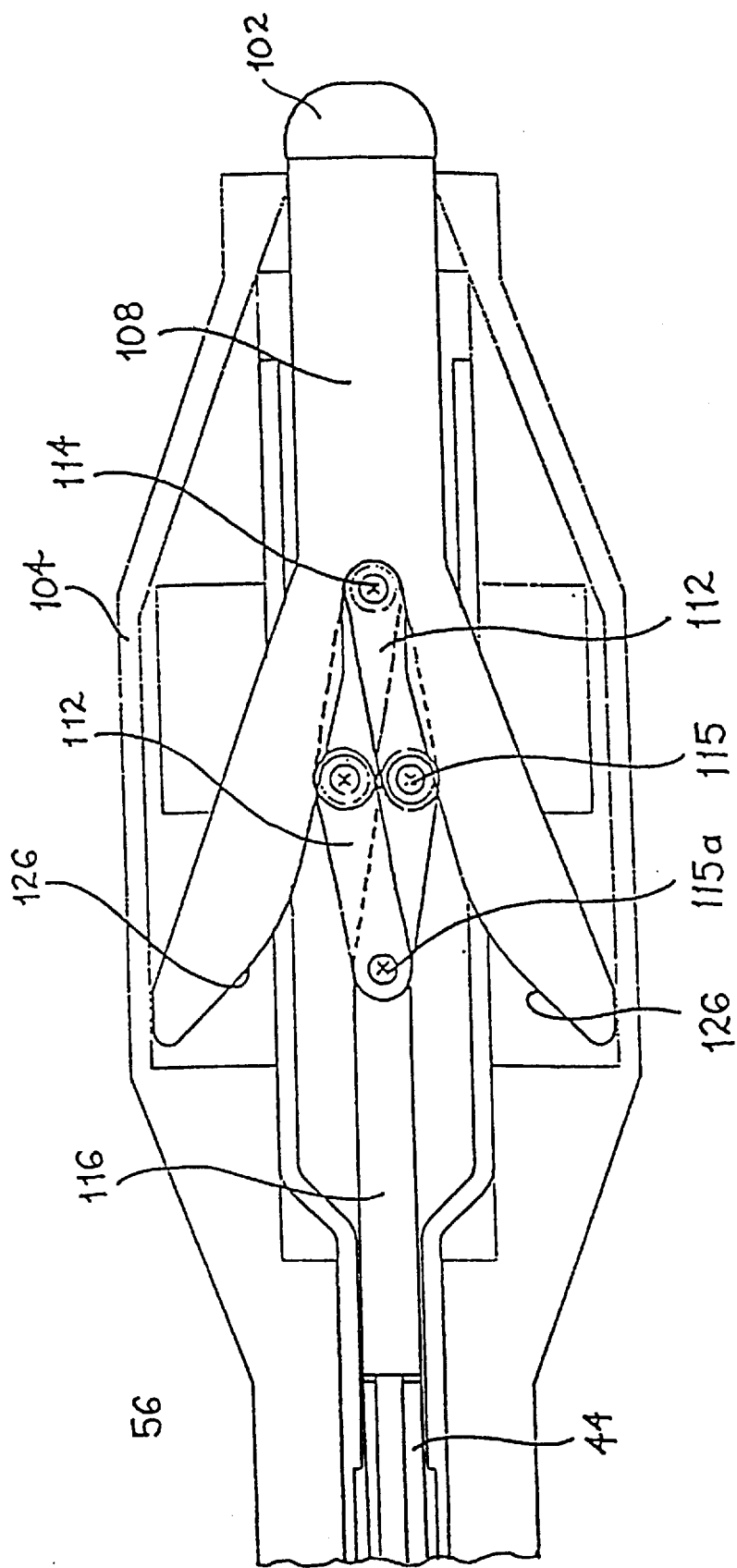
FIG. 13 illustrates a top plan cutaway view of the device of FIG. 10 showing the linkage arrangement of the adjustable closure mechanism of the present invention in a fully deployed condition.

In use, push button 102 is urged distally towards housing 103 so that camming surfaces 126 engage movable pivot posts 115. As linkage structure 110 collapses to the position shown in FIG. 13, movable pivot point 115A urges movable rod forwardly through retaining mechanism 101 to move fastener driver 56 and cartridge flame 44 distally to selectively position the jaw mechanism. When push button 102 is in the position shown in FIG. 13, linkage structure 110 is fully collapsed as shown and movable rod 116 is frictionally secured by clamp member 122.

As seen in FIG. 11, a handle locking mechanism 130 may also be provided. To fire the device to drive fasteners through tissue positioned in jaw mechanism 118, locking mechanism 130 is pivoted away from actuating handle 114 and the fasteners are driven through the tissue in the manner described above. To return instrument 100 to the position shown in FIG. 11, release knob 106 is moved in the direction of arrow H so that clamp member 122 is pivoted about shoulder 120. When clamp member 122 reaches a substantially vertical position perpendicular to movable rod 116, the frictional engagement between the central bore 128 and the movable rod 116 is released, and movable rod 116 returns to the position shown in FIG. 11 due to a biasing spring which is not shown. Release knob 106 is then let go of, and biasing spring 124 returns clamp member 122 to the position shown in FIG. 11. Linkage structure 110 returns to the position shown in FIG. 12.

As described above in connection with linkage structure 42, movement of linkage structure 110 provides for a two-stage approximation of the jaw mechanism, providing for a large approximation (about 80% of the total distance) of the jaw distance for movement of the first 50% of the slider mechanism 108. The remaining 50% of the movement of the slider mechanism 108 moves the jaw mechanism 18 its remaining 20% of distance, providing for fine adjustment.

The adjustable closure mechanism of the present invention can also be used in other instruments to close the distance between the movable jaw member and stationary jaw member at the stapling or fastening end of the instrument or between two movable jaw members. That is the jaw mechanism may be of the type, wherein one jaw moves toward and away from the other; however, the present invention is also applicable for use with devices of alternative types, i.e., where both jaws move toward and away from each other. The surgical instrument may be of the type which applies metal staples or two part fasteners of the bioabsorbable type.

The surgical stapling or fastening instrument employing the adjustable closure mechanism of the present invention is a device which may be operated with one hand to effect the closure motion of the jaw members of the instrument followed by activation of the trigger mechanism to fire the staples or fasteners into the tissue. The complex rotational or pivoting arrangement of the prior art devices is eliminated, resulting in a lightweight and easy to handle instrument which is inexpensive to manufacture and easy to assemble.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. An apparatus for applying surgical fasteners to body tissue, comprising:

tissue gripping means for positioning and gripping tissue therebetween, said tissue gripping means including a first jaw member having a plurality of fasteners positioned thereon, and a second jaw member;

means for driving said fasteners into said tissue;

trigger means for actuating said driving means;

means for advancing said first jaw member from a proximal position towards said second jaw member to a distal position in preparation for driving said fasteners into said tissue, said advancing means further advancing said driving means;

means for releasably retaining said advancing means to selectively position said first jaw member at multiple positions between said proximal and distal positions; and means for coupling said driving means to said actuating means, said driving means driving said fasteners only when said first jaw member is approximated a predetermined distance towards said second jaw member.

2. An apparatus according to claim 1, wherein said coupling means comprises a bearing surface on said driving means for engaging an arm member of said actuating means for driving said fasteners when said first jaw member is at said predetermined distance.

3. An apparatus according to claim 2, wherein said bearing surface comprises a notch for engaging said arm member, said notch extending from a sliding surface on said driving means upon which said arm rides prior to engaging said notch.

4. An apparatus according to claim 1, wherein the means for releasably retaining said advancing means includes:

a pivotable clamp member having a central bore through which a stationary rod passes, the retaining mechanism being coupled to the advancing means and being slidable over the stationary rod, the pivotable clamp member being movable to engage the stationary rod to selectively position the first and second jaws in relation to each other.

5. An apparatus according to claim 4 further including a release mechanism including a release rod, the release rod being operably associated with the retaining mechanism and movable to disengage the clamp member from the stationary rod to release the advancing means and the first jaw.

6. In a surgical apparatus for applying surgical fasteners to body tissue, said apparatus including actuating means at a proximal end, tissue gripping jaw members at a distal end, one of said jaw members having a plurality of fasteners positioned thereon, means for advancing said jaw members towards each other from spaced positions to approximated positions to grip tissue therebetween prior to driving said fasteners into said tissue, and fastener driving means for driving said fasteners into said tissue subsequent to positioning said jaws in response to movement of said advancing means, the improvement which comprises:

releasable means for retaining said advancing means to selectively retain said jaw members at multiple positions between said spaced and approximated positions prior to driving said fasteners into said tissue.

7. The surgical apparatus according to claim 6, wherein said retaining means comprises a pivotable clamp member.

8. The surgical apparatus according to claim 7, wherein said retaining means comprises a pivotable clamp member having a central bore through which said advancing means passes, an edge of said central bore engaging said advancing means to retain said advancing means and selectively position said jaw members in relation to each other.

9. The surgical apparatus according to claim 6, further comprising means for coupling said actuating means to said fastener driving means, said driving means driving said fasteners only when said jaw members are approximated a predetermined distance from each other following advancing said advancing means.

10. The surgical apparatus according to claim 9, wherein said coupling means comprises an arm member extending from said actuating means, said coupling means further comprising a notch in said driving means, said arm member engaging said notch when said jaw members are at said predetermined distance.

11. The surgical apparatus according to claim 6, wherein said retaining means comprises a pivotable clamp member having a central bore through which a fixed guide rod passes, said retaining means being coupled to said advancing means and slidable over said guide rod to releasably grasp said guide rod to retain said advancing means and selectively position said jaw members in relation to each other.

12. The surgical apparatus according to claim 11, further comprising means for releasing said clamp member, said release means pivoting said clamp member to a position substantially perpendicular to said guide rod to release said advancing means and said jaw member.

13. The surgical apparatus according to claim 12, wherein said clamp member is biased into an engaged position to retain said advancing means.

14. An apparatus for applying surgical fasteners to body tissue comprising:

a first jaw for carrying a plurality of fasteners;

a second jaw positioned opposite said first jaw;

means for approximating said first jaw from a proximal position towards said second jaw to a distal position to clamp body tissue therebetween;

means for driving said fasteners, said driving means including a bearing surface and being connected to said approximating means such that distal movement of said approximating means causes distal movement of said driving means, said bearing surface having a notch formed therein; and means for engaging said notch of said bearing surface of said driving means only when said first jaw has been approximated a sufficient distance towards said second jaw.

15. An apparatus according to claim 14, said engaging means comprising a lever having a distal end engageable with said notch.

16. An apparatus according to claim 15, further comprising trigger means for actuating said driving means, said lever connected to said trigger means.

17. An apparatus according to claim 16, wherein said lever remains substantially stationary during approximating of said first jaw.

18. An apparatus according to claim 17, wherein said lever is held in a position out of engagement with said notch by said driving means.

19. An apparatus according to claim 18, wherein said bearing surface is formed at a proximal end of said driving means.

20. An apparatus according to claim 14 further including a means for releasably retaining said approximation means wherein said retaining means includes a pivotable clamp member having a central bore through which a stationary rod passes, the retaining means being coupled to the approximating means and being slidable over the stationary rod, the pivotable clamp being movable to engage the stationary rod to selectively position the first and second jaws in relation to each other.

21. An apparatus according to claim 20 further including a release mechanism including a release rod, the release rod being operably associated with the retaining mechanism and movable to disengage the clamp member from the stationary rod to release the approximating means and the first jaw.

22. An apparatus for applying surgical fasteners to body tissue comprising:
a housing;
a first jaw carrying a plurality of fasteners;
a second jaw positioned opposite the first jaw;
a slider mechanism having a proximal end extending through the housing and a distal end operably connected to the first jaw, the proximal end of the slider mechanism being linearly movable to advance the first jaw towards the second jaw to clamp body tissue therebetween;
a fastener driver movable with respect to the first jaw;
an actuating handle; and
a coupling arm movable from a first position preventing ejection of the fasteners to a second position operably connecting the actuating handle to the fastener driver, the coupling arm being movable to the second position only when the first jaw is advanced a predetermined distance from the second jaw to enable ejection of the fasteners.

23. An apparatus according to claim 22, wherein the fastener driver is operably connected to the slider mechanism such that the driver is advanced towards the second jaw when the slider mechanism is moved to advance the first jaw towards the second jaw.

24. An apparatus according to claim 23, wherein the fastener driver comprises a bearing surface having a notch, the coupling arm being movable to engage the notch when the first jaw member has been advanced to the predetermined distance from the second jaw.

25. An apparatus according to claim 24, wherein the coupling arm includes a distal end positioned to ride along the bearing surface as the fastener driver is advanced by the slider mechanism.

26. An apparatus according to claim 22 further comprising a retaining mechanism operably associated with the slider mechanism to selectively position the first jaw in relation to the second jaw.

27. An apparatus according to claim 26 wherein the retaining mechanism comprises a pivotable clamp member having a central bore through which a stationary rod passes, the retaining mechanism being coupled to the slider mechanism and slidable over the stationary rod, the pivotable clamp being movable to engage the stationary rod to selectively position the first and second jaws in relation to each other.

28. An apparatus according to claim 27 further comprising a release mechanism including a release rod, the release rod being operably associated with the retaining mechanism and movable to disengage the clamp member from the stationary rod to release the slider mechanism and the first jaw.

29. An apparatus for applying surgical fasteners to body tissue comprising:
first and second jaws, the first jaw having a plurality of fasteners positioned thereon and being movable in relation to the second jaw;
an advancing mechanism operably connected to the first jaw, the advancing mechanism being movable to advance the first jaw towards the second jaw;
a retaining mechanism operably associated with the advancing mechanism, the retaining mechanism selectively positioning the first jaw in relation to the second jaw;
a fastener driver movably positioned in relation to the first jaw and including a bearing surface; and
an actuating mechanism including a coupling arm, the coupling arm being linearly movable relative to the bearing surface from a first position preventing ejection of the fasteners to a second position operatively engaging the driver, the coupling arm being movable to the second position only when the first jaw has been advanced a predetermined distance from the second jaw.

30. An apparatus according to claim 29, wherein the bearing surface includes a notch formed therein.

31. An apparatus according to claim 30 wherein the driver is operably associated with the advancing mechanism such that the driver is advanced towards the second jaw when the advancing mechanism is moved to advance the first jaw towards the second jaw.

32. An apparatus according to claim 31 wherein the coupling arm remains substantially stationary during advancement of the first jaw by the advancing mechanism, the coupling arm being positioned to ride along the bearing surface and to engage the notch only when the first jaw has been advanced to the predetermined distance from the second jaw.

33. An apparatus according to claim 32 wherein the coupling arm includes a distal tip positioned to engage the notch when the first jaw has been advanced the predetermined distance from the second jaw.

34. An apparatus according to claim 30, wherein the bearing surface is formed on a proximal end of the driver.

35. An apparatus according to claim 29 wherein the retaining mechanism comprises a pivotable clamp member having a central bore through which a stationary rod passes, the retaining mechanism being coupled to the advancing mechanism and slidable over the stationary rod, the pivotable clamp being movable to engage the stationary rod to selectively position the first and the second jaws in relation to each other.

36. An apparatus according to claim 35 further comprising a release mechanism including a release rod, the release rod being operably associated with the retaining mechanism and movable to disengage the clamp from the stationary rod to release the advancing mechanism and the first jaw.

37. An apparatus for applying surgical fasteners to body tissue, comprising:

a housing;

a first jaw carrying a plurality of fasteners;

a second jaw positioned opposite the first jaw;

a slider mechanism extending from the housing and being operably connected to the first jaw and linearly movable to advance the first jaw towards the second jaw to clamp body tissue therebetween;

a driver movable with respect to the first jaw;

an actuating handle operably connected to the driver, wherein movement of the actuating handle advances the driver and effects ejection of the fasteners; and a mechanism operably connected to the actuating handle to prevent ejection of the fasteners until the first jaw has been positioned a predetermined distance from the second jaw.

38. An apparatus according to claim 37 further including a retaining mechanism including a pivotable clamp member having a central bore through which a stationary rod passes, the retaining mechanism being coupled to the slider mechanism and slidable over the stationary rod, the pivotable clamp being movable to engage the stationary rod to selectively position the first and second jaws in relation to each other.

39. An apparatus according to claim 38 further including a release mechanism including a release rod, the release rod being operably associated with the retaining mechanism and movable to disengage the clamp member from the stationary rod to release the slider mechanism and the first jaw.

* * * * *